(12) United States Patent
Yang et al.

(10) Patent No.: US 6,911,021 B2
(45) Date of Patent: Jun. 28, 2005

(54) SAFETY SYRINGE FOR TAKING BLOOD

(76) Inventors: Jih-Hsiung Yang, No. 822, Chungcheng Rd., Wufeng Hsiang, Taichung Hsien (TW); Hsiu-Chih Lin, No. 1, Tatung Rd., Pentang Village, Wufeng Hsiang, Taichung Hsien (TW)

( * ) Notice: Subject to any disclaimer, the term of this patent is extended or adjusted under 35 U.S.C. 154(b) by 141 days.

(21) Appl. No.: 10/453,383

(22) Filed: Jun. 3, 2003

(65) Prior Publication Data
US 2004/0249309 A1 Dec. 9, 2004

(51) Int. Cl.[7] .................. A61M 5/00; A61M 37/00; A61B 19/00
(52) U.S. Cl. .................. 604/191; 604/131; 604/90; 604/88; 604/211; 600/575
(58) Field of Search .................. 604/191, 131, 604/249, 72, 90–82, 237, 181, 211, 138, 205, 187; 222/137; 141/18, 309; 600/575

(56) References Cited

U.S. PATENT DOCUMENTS

| | | | | |
|---|---|---|---|---|
| 4,610,666 A | * | 9/1986 | Pizzino | 604/191 |
| 5,199,949 A | * | 4/1993 | Haber et al. | 604/88 |
| 5,298,023 A | * | 3/1994 | Haber et al. | 604/90 |
| 5,314,412 A | * | 5/1994 | Rex | 604/191 |

* cited by examiner

Primary Examiner—Nicholas D. Lucchesi
Assistant Examiner—Roz Maiorino
(74) Attorney, Agent, or Firm—William E. Pelton, Esq.

(57) ABSTRACT

A safety syringe for taking blood has a hollow barrel, a seal, a tube and a needle hub. The hollow barrel has an outside surface, a proximal open end and a distal closed end. The seal with an inner needle is mounted inside the hollow barrel. The tube has a proximal open end and a distal open end and is attached longitudinally to the outside surface of the hollow barrel. The needle hub is mounted inside the tube, and the needle can extend out of the distal open end of the tube. A first through hole defined in the hollow barrel and a second through hole is defined in the tube align with the first through hole. When taking blood, the needle is extended out from the distal end of the tube to take a blood sample and a vacutainer is inserted into the hollow barrel to collect a blood sample. The used needle is retracted into the tube after use to keep people from getting injured or infected.

7 Claims, 6 Drawing Sheets

SAFETY SYRINGE FOR TAKING BLOOD

BACKGROUND OF THE INVENTION

1. Field of the Invention

The present invention relates to a syringe, and more particularly to a safety syringe that can safely hold a used needle and prevent users from getting hurt by the used needle.

2. Description of Related Art

There are two types of conventional syringes used for taking blood, one has a hollow barrel, a plunger and a needle hub, and the other has a short holder, an inner needle and a needle hub. The plunger of the first type is received inside the hollow barrel, and the needle hub is connected to the hollow barrel. The short holder of the second type has an outside surface, a bottom surface and an inner space. The needle hub is mounted on the bottom surface of the outside surface and the inner needle mounted on inner space and connects to the needle hub.

When using the first type of the conventional syringe, a user takes blood into the hollow barrel then inserts the collected blood into a vacuum tube. When using the second type of the conventional syringe, the needle hub is inserted into a vein and a vacutainer is connected to the inner needle inside the short holder. Because of the attraction of the vacutainer and the blood pressure, blood will flow into the vacutainer slowly.

However, the used needles extended outside the hollow barrel or the short holder of the conventional syringes are easily hurt users after taking blood. To keep nurses, doctors or health workers who deal with discarded syringes from getting injured or infected by used needles, a safety syringe for taking blood is needed. In another aspect, the short holder of the second conventional syringe is too easily reused to hold a new needle and unscrupulous staff may be tempted to reduce costs in this way whereby serious unsanitary conditions will be met.

To overcome the shortcomings of conventional syringes, the present invention provides a safety syringe to mitigate or obviate the aforementioned problem.

SUMMARY OF THE INVENTION

The primary objective of the present invention is to provide a safety syringe for taking blood. The safety syringe for taking blood in accordance with the present invention comprises a hollow barrel, a seal, a tube and a needle hub.

The hollow barrel has a proximal open end, a distal closed end, an outside surface, a dovetail keyway and a first through hole. The seal with an inner needle is mounted inside the hollow barrel. The tube has a proximal open end and a distal open end and is mounted on the hollow barrel. The needle hub and a spring are mounted inside the tube, and the needle selectively extends from the proximal open end of the tube. The first through hole is defined in the hollow barrel through the dovetail keyway, and a second through hole is defined in the tube. The first through hole faces the second through hole.

When using the syringe in accordance with the present invention, the needle hub extends out of the tube to draw a blood sample and a vacutainer is inserted into the hollow barrel to collect blood sample. When taking a blood sample is finished, the used needle hub is retracted inside the tube to keep the used needle from injuring or infecting a person.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
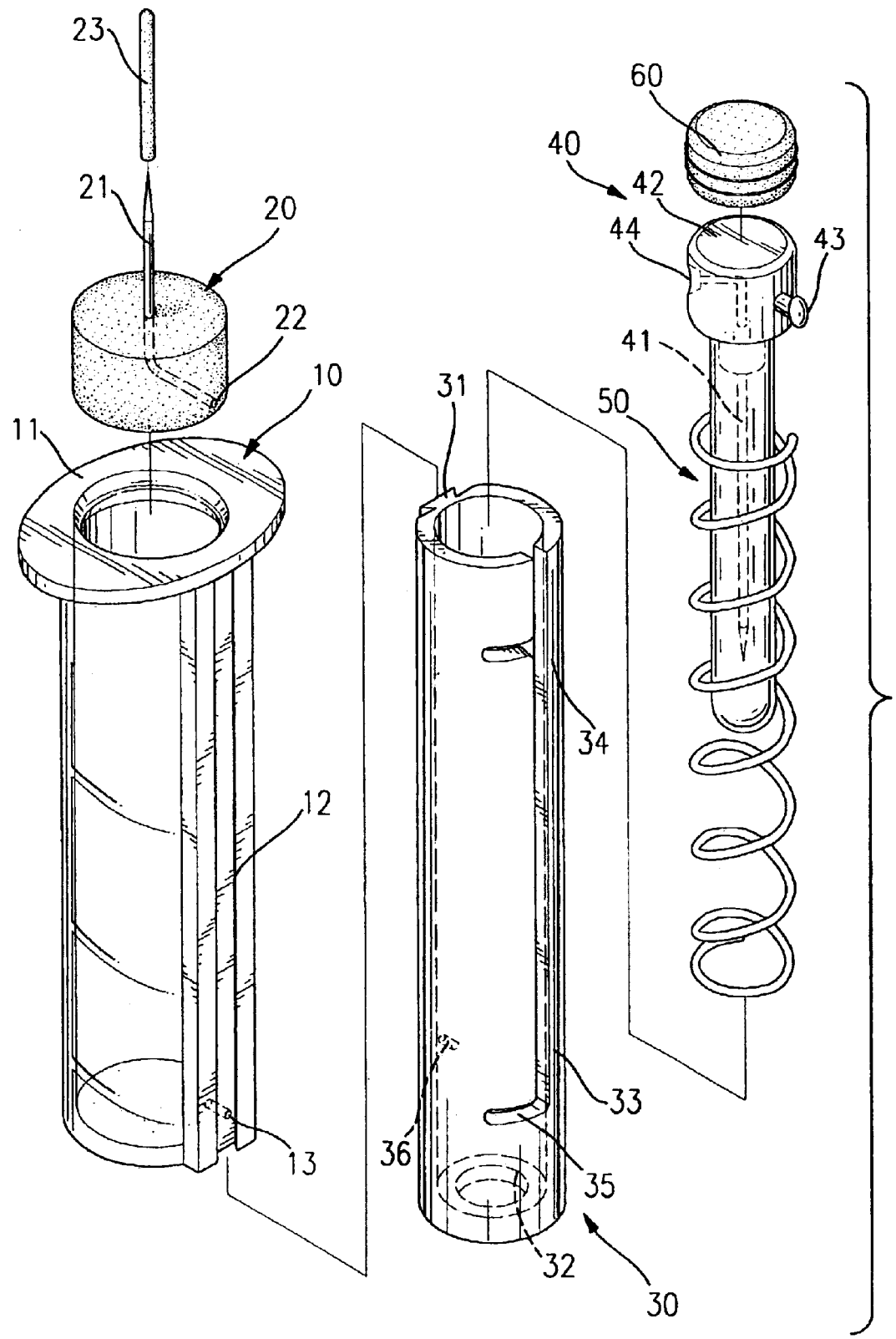
FIG. 1 is an exploded perspective view of a first embodiment of a safety syringe for taking blood in accordance with the present invention.
Figure 2:
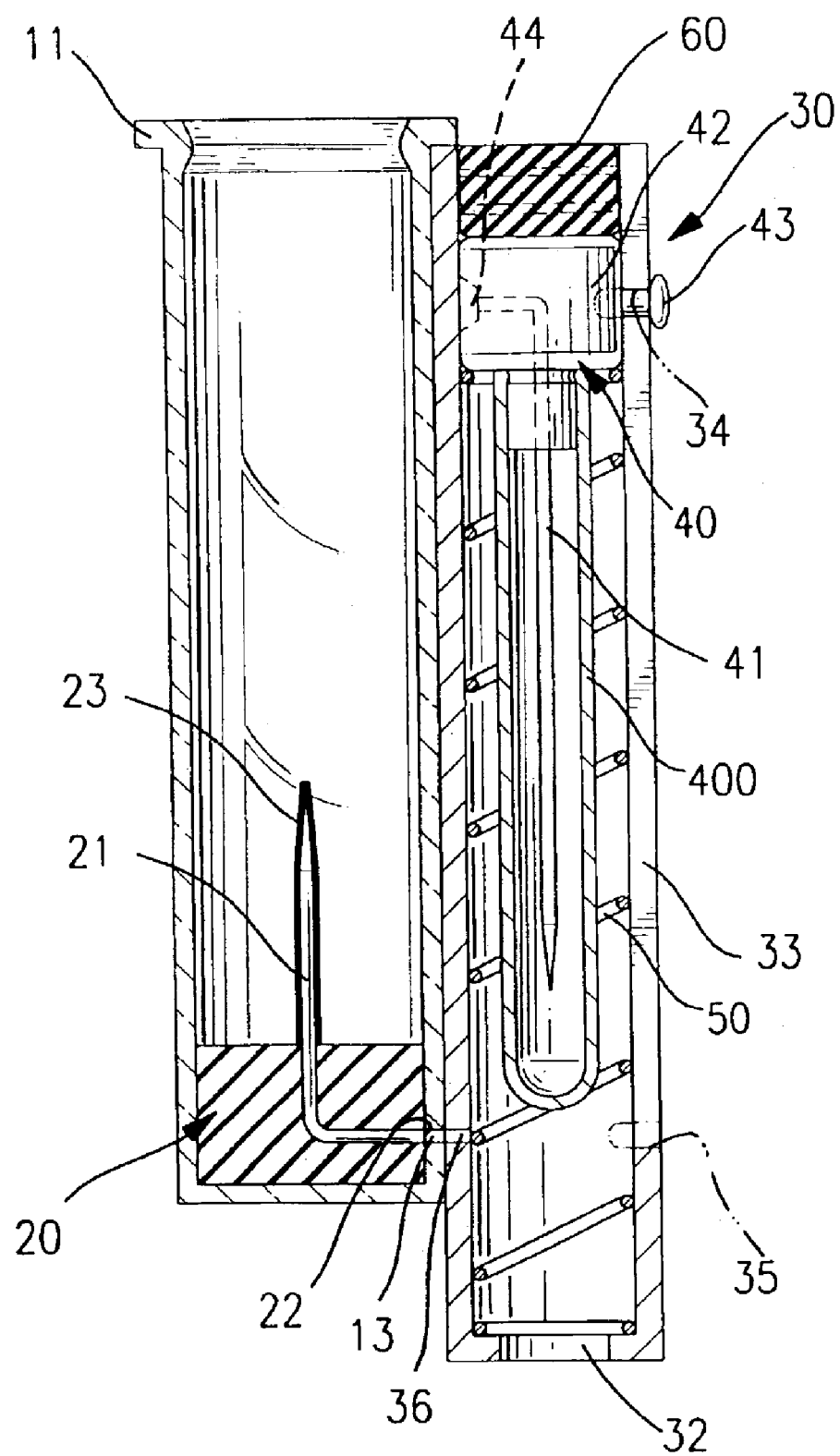
FIG. 2 is a side plan view in partial section of the safety syringe for taking blood in FIG. 1 with a covered needle in the tube.

With reference to FIGS. 1 and 2, a safety syringe of a first embodiment in accordance with the present invention has a hollow barrel (10), a seal (20), a tube (30) and a needle hub (40):

The hollow barrel (10) is cylindrical and has a distal closed end (not numbered), a proximal open end (not numbered), a sidewall (not numbered), an outside surface (not numbered), an annular flange (11), a dovetail keyway (12) and a first through hole (13). The annular flange (11) is defined radially around and extends out from the proximal open end. The dovetail keyway (12) is formed longitudinally on the outside surface of the hollow barrel (10). The first through hole (13) is defined through the sidewall in the dovetail keyway (12) near the distal closed end.

Figure 5:
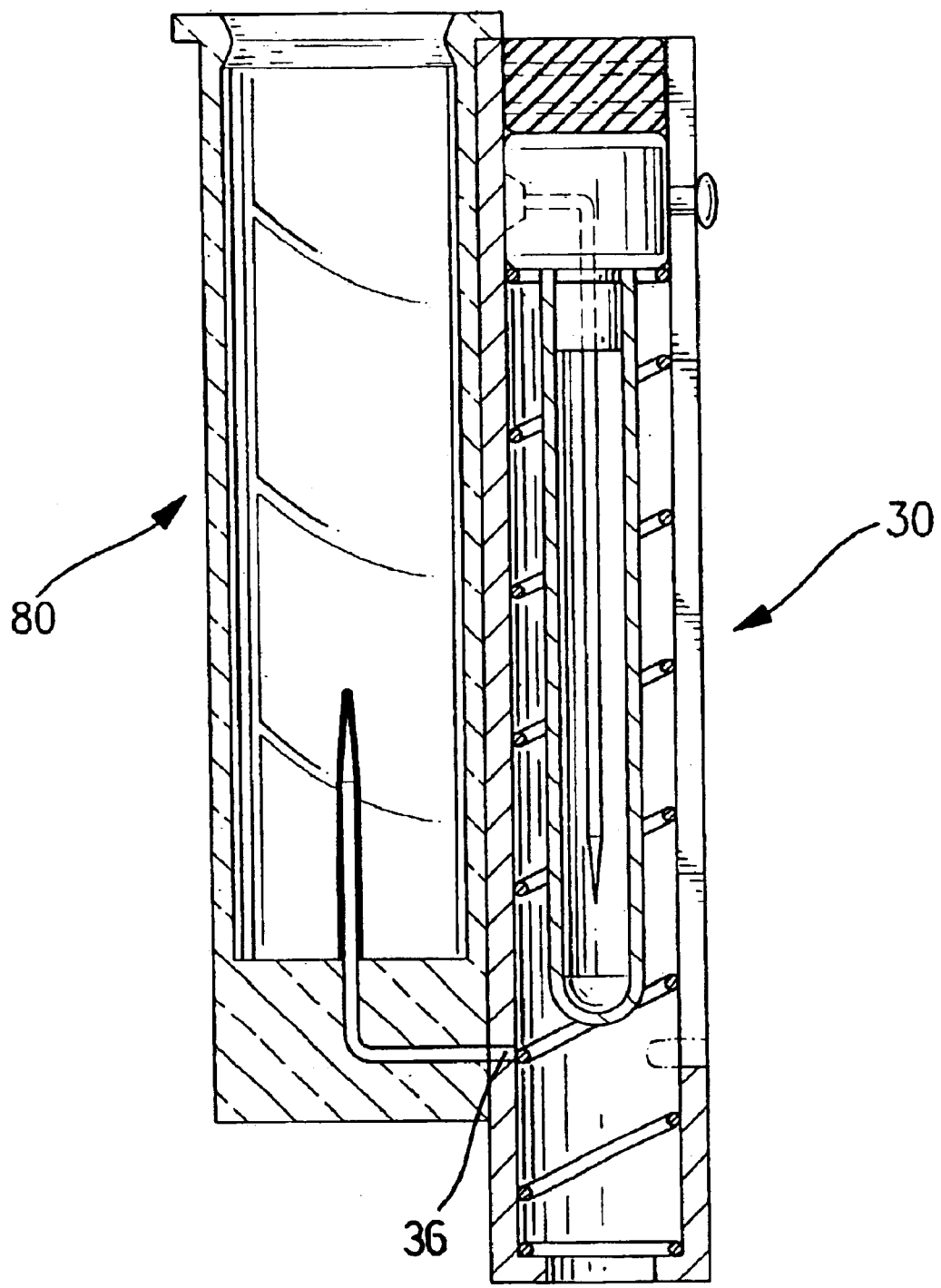
FIG. 5 is a side plan view in partial sectional of a second embodiment of the safety syringe for taking blood in accordance with the present invention.

The seal (20) has a proximal end (not numbered), a distal end (not numbered), an inner needle (21) and an elastic sheath (23) and is mounted inside the distal end of the hollow barrel (10). The inner needle (21) is L-shaped with an inner channel and has a proximal end (not numbered) and a distal end (not numbered). The distal end is perpendicular to the proximal end and is mounted inside the seal (20) and the inner channel defines a hole (22) at the distal end forms an egress in the seal (20). The elastic sheath (23) is mounted on the inner needle (21). With further reference to FIG. 5, a second embodiment of the safety syringe for taking blood is shown, wherein the seal also can be inside the hollow barrel (80) in other ways such as integrally formed together with the hollow barrel (80).

Figure 6:
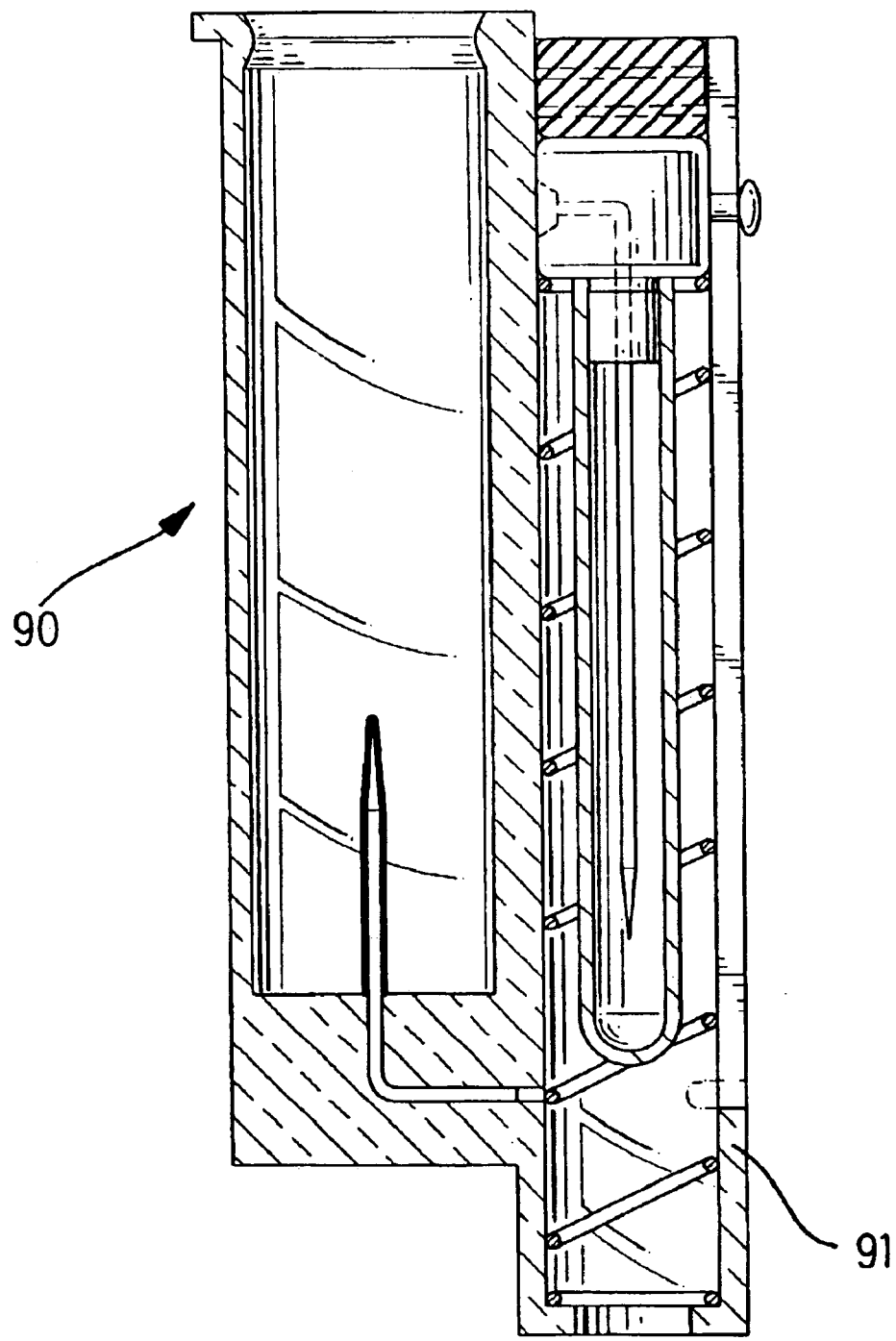
FIG. 6 is a side plan view in partial sectional of a third embodiment of the safety syringe for taking blood in accordance with the present invention.

The tube (30) is connected to the hollow barrel (10) and has an outside surface (not numbered), a dovetail key (31), a lip (32), a distal open end (not numbered), a proximal open end (not numbered), a guide slot (33), a sidewall (not numbered) and a second through hole (36). The dovetail key (31) is formed longitudinally on and extends from the outside surface and engages the dovetail keyway (12) on the hollow barrel (10). The lip (32) is formed at the distal open end and protrudes radially inward so that the diameter of the distal open end is smaller than the proximal open end. The guide slot (33) has a proximal end (not numbered), a distal end (not numbered), a retracted locking slot (34) and an extended locking slot (35) and is defined longitudinally through the sidewall of the tube (30) diametrically opposite from the dovetail key (31). The proximal end of the guide slot (33) can be open and is at the proximal open end of the tube (30). The retracted locking slot (34) is formed near the proximal end of and perpendicular to the guide slot (33). The extended locking slot (35) is formed at the distal end of and perpendicular to the guide slot (33). The second through hole (36) is defined through sidewall of the tube (30) and the dovetail key (31) and faces and aligns with the first through hole (13) defined through the hollow barrel (10). With further reference to FIG. 6, a third embodiment of the safety syringe is shown, wherein the tube (91) also can connect to the hollow barrel (90) in other ways such as being integrally formed together with the hollow barrel (90). As shown in FIGS. 5 and 6, the seal in each of the embodiments of FIGS. 5 and 6 is integrally formed together with the hollow barrels 80 and 90 respectively.

The safety syringe in accordance with the present invention further comprises a spring (50) and a plug (60). The spring.(50) has a distal end (not numbered) and a proximal end (not numbered) and is inserted into the tube (30). The distal end of the spring (50) abuts the lip (32) in the distal open end of the tube (30).

Figure 3:
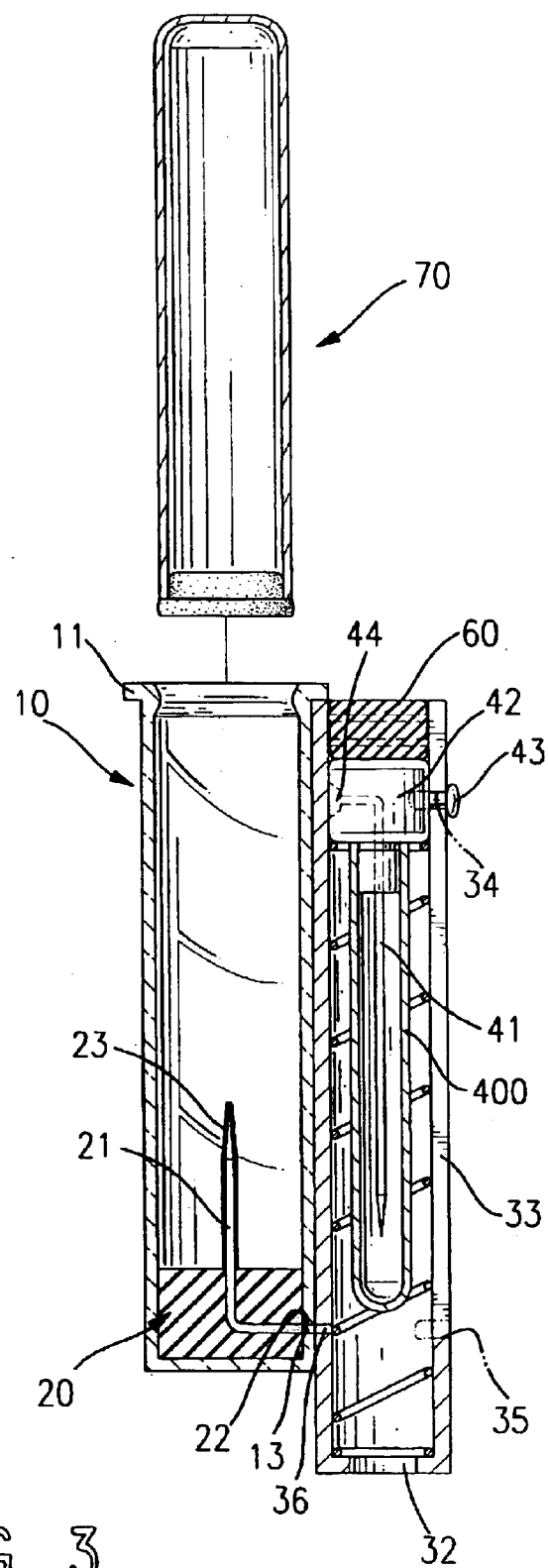
FIG. 3 is an operational side plan view in partial section of the safety syringe for taking blood in FIG. 1 with a vacutainer.
Figure 4:
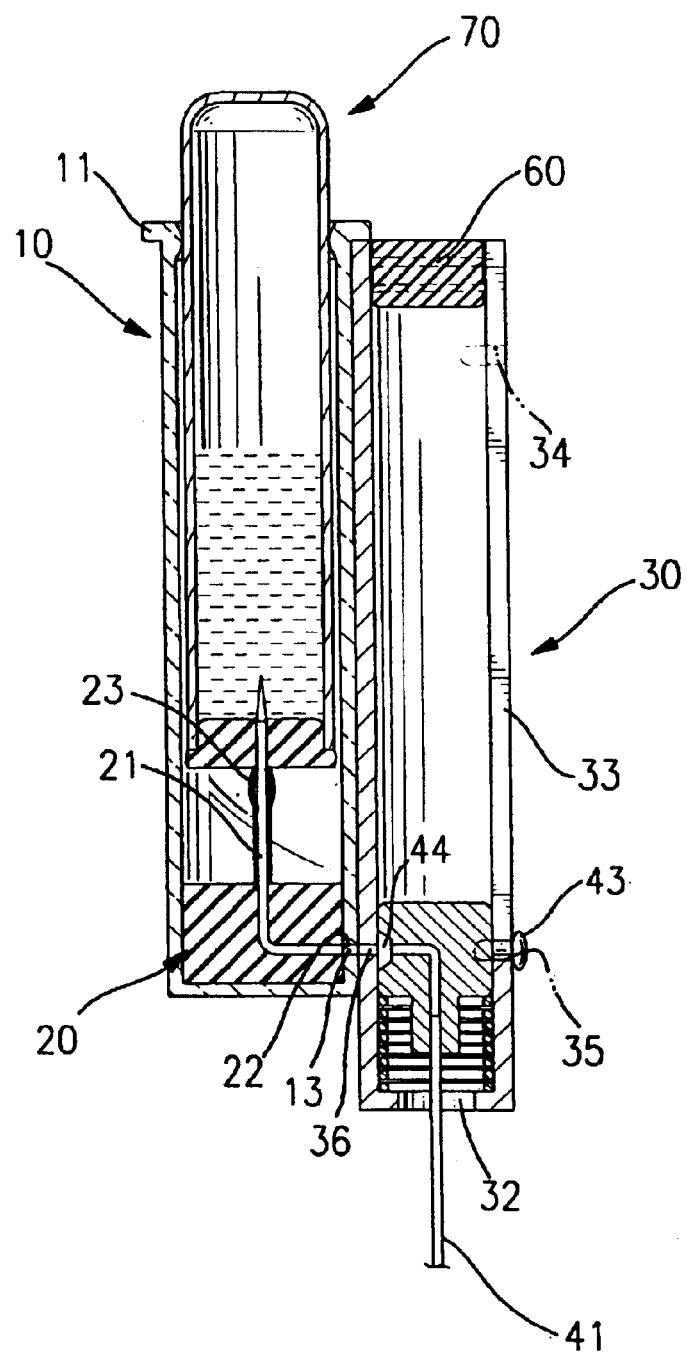
FIG. 4 is an operational side plan view in partial section of the safety syringe for taking blood in FIG. 1 with the needle extended out the tube and the inner needle is inserted into the vacutainer.

The needle hub (40) is slidably mounted inside the tube (30) and has a needle (41), a stopper (42), a guide stub (43), a fluid channel (not numbered) and a tapered hole (44). The stopper (42) is cylindrical and has a top surface (not numbered), a bottom surface (not numbered) and a cylindrical surface (not numbered). The bottom surface abuts the lip (32) of the tube (30). The needle (41) has a longitudinal fluid passage (not shown), and passes through the spring (50) and is mounted in the bottom surface of the stopper (42). The fluid channel has a first end (not numbered) and a second end (not numbered). The first end is extended through the bottom surface of the stopper (42), and the second end is extended through the cylindrical surface of the stopper (42). The first end of the fluid channel is connected to the needle (41), and the second end of the fluid channel is connecting to the tapered hole (44) that is formed in the cylindrical surface. With further reference to FIGS. 3 and 4, the guide stub (43) is attached to the cylindrical surface of the stopper (42) so the tapered hole (44) aligns with the second through hole (36) when the guide stub (43) is fully seated in the extended locking slot (35).

The needle hub (40) may optionally include a needle cap (400). The needle cap (400) is detachably attached to the bottom surface of the stopper (42) to cover the needle (41) to protect the needle (41) from contaminants and to keep the needle (41) from injuring a person when the needle (41) is being extended from the tube (30). The needle cap (400) is removed from the needle (41) and discarded to draw a blood sample into a vacutainer (70) inside the hollow barrel (10).

The plug (60) is cylindrical and is mounted securely inside the distal open end of the tube (30) to hold the needle hub (40) inside the tube (30).

With reference to FIGS. 3 and 4, when taking blood from a patient's body, the user moves the stopper (42) from the retracted locking slot (34) to the guide slot (33) by means of holding the guide stub (43). The stopper (42) is slid toward the distal end of the guide slot (33) and is moved into the extended locking slot (35) to hold the needle (41) outside the distal open end of the tube (30) and to align the tapered hole (44) with the second through hole (36) in the tube (30). The spring (50) is compressed between the lip (32) at the proximal open and the bottom surface of the needle hub (40).

The vacutainer (70) is inserted toward the proximal end of the hollow barrel (10) and the elastic sheath (23) is pushed toward the seal (20) so a blood sample can be drawn through the needle (41), the fluid channel, the second through hole (36) and the first through hole (13) of the hollow barrel (10), and then into the vacutainer (70).

The guide stub (43) is released from the extended locking slot (35), and the spring (50) pushes the guide stub (43) toward the proximal end of the guide slot (33). The spring (50) also holds the needle hub (40) and the needle (41) in the tube (30).

The needle hub (40) of the safety syringe for taking blood in accordance with present invention can be retracted inside the tube (30) so that the used needle (41) will not injure users or contaminate the users. Also, the safety syringe for taking blood can be discarded and prevents the used hollow barrel (10) from being reused.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe for taking blood comprising
   a hollow barrel having
      a distal closed end;
      a proximal open end;
      a sidewall;
      an outside surface; and
      a first through hole defined through the sidewall;
   a seal mounted inside the hollow barrel;
      an inner needle being L-shaped with an inner channel and mounted on the seal;
   a tube connected to the hollow barrel, being cylindrical and having
      a proximal open end;
      a distal open end;
      a sidewall;
      a lip defined inside the distal open end;
      a guide slot defined longitudinally through the tube and having a proximal end and a distal end;
      two locking slots defined through the tube and locking slots being perpendicular to the guide slot and communicating with the guide slot;
      a second through hole defined through the sidewall of the tube and aligning and communicating with the first through hole of the hollow barrel; and
   a needle hub slidably mounted inside the tube and having
      a stopper having a top surface, a bottom surface and a cylindrical surface;
      a needle with a longitudinal fluid passage and mounted in the bottom surface of the stopper;
      a fluid channel defined through the stopper and having
         a first end defined through the bottom surface of the stopper and connected to the needle; and
         a second end;
      a guide stub attached to the cylindrical surface of the stopper and moveably received in the guide slot in the tube; and
      a tapered hole formed in the cylindrical sidewall and communicating with the second end of the fluid channel so the tapered hole aligns with the second through hole when the needle of the needle hub is fully extended out the tube.

2. The safety syringe for taking blood as claimed in claim 1, wherein the hollow barrel and the tube are integrally formed together.

3. The safety syringe for taking blood as claimed in claim 1, wherein the seal and the hollow barrel are integrally formed together.

4. The safety syringe for taking blood as claimed in claim 1 further comprises a spring mounted inside the tube and the needle is inserted through the spring.

5. The safety syringe for taking blood as claimed in claim 4 further comprises a plug mounted inside the proximal open end of the tube.

6. The safety syringe for taking blood as claimed in claim 1, wherein the locking slots comprises a retracted locking slot formed near the proximal end of and perpendicular to the guide slot, and an extended locking slot is formed at the distal end of and perpendicular to the guide slot.

7. The safety syringe for taking blood as claimed in claim 1, wherein the inner needle further comprises an elastic sheath mounted on the inner needle.

* * * * *